United States Patent
Tomimori et al.

(10) Patent No.: US 8,653,040 B2
(45) Date of Patent: Feb. 18, 2014

(54) COMPOSITIONS CONTAINING SESAMIN-CLASS COMPOUND(S) AND QUERCETIN GLYCOSIDE(S)

(75) Inventors: Namino Tomimori, Osaka (JP); Yoshiko Ono, Osaka (JP)

(73) Assignee: Suntory Holdings Limited, Osaka-shi, Osaka (JP)

(*) Notice: Subject to any disclaimer, the term of this patent is extended or adjusted under 35 U.S.C. 154(b) by 467 days.

(21) Appl. No.: 12/810,635

(22) PCT Filed: Dec. 19, 2008

(86) PCT No.: PCT/JP2008/073206
§ 371 (c)(1),
(2), (4) Date: Aug. 13, 2010

(87) PCT Pub. No.: WO2009/084482
PCT Pub. Date: Jul. 9, 2009

(65) Prior Publication Data
US 2010/0311676 A1    Dec. 9, 2010

(30) Foreign Application Priority Data
Dec. 28, 2007   (JP) ................................. 2007-338853

(51) Int. Cl.
*A01N 43/04*    (2006.01)

(52) U.S. Cl.
USPC .................. 514/27; 426/648; 426/590; 536/8

(58) Field of Classification Search
USPC .......................... 514/27; 426/590, 648; 536/8
See application file for complete search history.

(56) References Cited

U.S. PATENT DOCUMENTS

| | | |
|---|---|---|
| 2008/0275110 A1 | 11/2008 | Ono et al. |
| 2010/0021614 A1 | 1/2010 | Nishijima et al. |

FOREIGN PATENT DOCUMENTS

| | | |
|---|---|---|
| JP | 05-058902 A | 3/1993 |
| JP | 10-273444 A | 10/1998 |
| JP | 11-106336 A | 4/1999 |
| JP | 2006-320341 | 11/2006 |
| JP | 2008-174553 | 7/2008 |
| JP | 2008/201763 | 9/2008 |
| WO | 2006/014028 | 2/2006 |
| WO | 2006/070856 | 7/2006 |

OTHER PUBLICATIONS

Moltke et al, J. Pharm. Pharmacol., 2004, 56, 1039-1044.*
Lee et al, Arch Pharm Res, 2002, 25(3), 280-284.*
Lopez et al, Talanta, 2003, 60, 609-616.*
Sumio et al, JP 1994-227977, published Aug. 16, 1994, Machine Translation.*
Bedir et al, J. Agric. Food. Chem., 2002, 50, 3150-3155.*
Washino, JP04-066099, published Mar. 2, 1992.*
M. Ye, et al., "Studies on Chemical Constituents of *Cuscuta chinensis*", (2002), Zhongguo Zhongyao Zazhi, 27:115-117, Accession No. 139:273675.
H. Guo et al., "Study on Constituents of the Seed from *Cuscuta australis*", (2000), Beijing Zhongyiyao Daxue Xuebao, 23:20-23, Accession No. 134:39497.
International Search Report mailed Mar. 10, 2009 in International PCT Application No. PCT/JP2008/073206 filed Dec. 19, 2008.
International Preliminary Report on Patentability issued Aug. 10, 2010, in PCT/JP2008/073206 filed Dec. 19, 2008.

* cited by examiner

*Primary Examiner* — Jason M Sims
*Assistant Examiner* — Ibrahim D Bori
(74) *Attorney, Agent, or Firm* — Drinker Biddle & Reath LLP (57) ABSTRACT

The purpose of the present invention is to provide a means of enhancing the bodily absorption of sesamin-class compounds. By using sesamin-class compounds and quercetin glycosides in combination, the bodily absorption of the sesamin-class compounds can be enhanced.

7 Claims, 4 Drawing Sheets

COMPOSITIONS CONTAINING SESAMIN-CLASS COMPOUND(S) AND QUERCETIN GLYCOSIDE(S)

CROSS REFERENCE TO RELATED APPLICATIONS

This application is a National Stage of International Application No. PCT/JP2008/073206 filed Dec. 19, 2008, and which claims benefit of Japanese Patent Application No. 2007-338853 filed Dec. 28, 2007, which are incorporated herein in their entirety.

TECHNICAL FIELD

The present invention relates to compositions for enhancing the bodily absorbability of sesamin-class compounds, agents for enhancing the bodily absorption of sesamin-class compounds, as well as foods and beverages or pharmaceutical compositions that utilize them.

BACKGROUND ART

Sesamin-class compounds are a class of lignan compounds that are contained in sesame. Among others, sesamin and its stereoisomer episesamin have been reported to have various physiological activities, including the action of lowering the blood cholesterol and the blood neutral lipid, the action of improving hepatic functions, the action of scavenging active oxygen, the action of inhibiting Δ5-desaturase, the action of suppressing the generation of lipid peroxides, the anti-hypertensive action, the action of preventing sickness from drinking, and the breast cancer suppressing action (Patent Document 1).

However, lignan-class compounds encompassing sesamin-class compounds are not merely hardly soluble in water but they are also soluble to only a certain extent in organic solvents that can be used in pharmaceutical or dietary applications. Because of such very low solubility, the lignan-class compounds have the problem that they cannot be easily absorbed into the body.

An example of the methods that have been disclosed for improving the bodily absorbability of fat-soluble substances comprises dissolving the fat-soluble substance ubidecarenone in edible natural oils or fats or in triglycerides of middle-chain fatty acids to make it in liquid form, thereby enhancing the bodily absorption of ubidecarenone (Patent Document 2).

Another method, that has been proposed for improving the bodily absorbability of fat-soluble substances, comprises reduction of the size of their micelles (making them in fine particles). For example, a coenzyme Q10 containing, water-soluble composition has been disclosed that is prepared from a composition comprising coenzyme Q10 and other specific components such as polyglycerol and fatty acid monoester and which has its average particle size reduced to 110 nm and less, whereby its bodily absorption is markedly improved (Patent Document 3). However, no case has been reported in which the bodily absorbability of sesamin-class compounds is improved by combining it with other compounds.

Patent Document 1: the pamphlet of WO 2006/070856
Patent Document 2: the official gazette of JP 54-92616 A
Patent Document 3: the official gazette of JP 2004-196781 A

DISCLOSURE OF THE INVENTION

Problems to be Solved by the Invention

When one uses the above-described means that are capable of enhancing the bodily absorption of fat-soluble substances, the fat-soluble substance has to be dissolved in oils or fats or the like so that it is in a liquid form or, alternatively, a liquid containing micelles of the fat-soluble substance has to be made. However, sesamin-class compounds have such a low solubility in oils or fats that if one wants to increase the amount of sesamin-class compounds that can be ingested at a time, the amount of oils or fats that serve as the solvent has also to be increased. This has posed a problem in that if sesamin-class compounds are formulated as preparations, the resulting preparations become too bulky and, particularly in the case where they are formulated as capsules or the like, too many number of them have to be ingested at a time. Another concern is the potential ingestion of excess calorific value that might result from ingesting increased amounts of oils or fats. On the other hand, in order to form micelles with a view to improving their absorbability, fat-soluble substances have to be emulsified uniformly and the need for a complicated process has contributed to a higher cost.

An object, therefore, of the present invention is to provide a new means for enhancing the bodily absorption of sesamin-class compounds, by which the above-described problems of the prior art can be solved.

Means for Solving the Problems

The present inventors conducted intensive studies with a view to solving the problems mentioned above and found that by using sesamin-class compounds in combination with quercetin glycosides, it becomes possible to enhancing the bodily absorption of the sesamin-class compounds.

Thus, the present invention relates to the following:

1. A composition containing at least one sesamin-class compound and at least one quercetin glycoside;
2. The composition as described in 1 above, wherein the total weight of the quercetin glycoside as calculated for quercetin is 0.3 or more, relative to the total weight of the sesamin-class compound which is taken as unity;
3. The composition as described in 1 or 2 above, wherein the sesamin-class compound is sesamin and/or episesamin;
4. The composition as described in any one of 1 to 3 above, wherein the quercetin glycoside is at least one member selected from the compounds represented by formula (I):

[Chemical Formula 1]

(where $(X)_n$ signifies a sugar chain, and n signifies an integer of 1 or more);

5. The composition as described in 4 above, wherein the quercetin glycoside is at least one member selected from the compounds which are represented by formula (II):

[Chemical Formula 2]

(II)

(where m is 0, or an integer of 1 or more), and consist of isoquercitrin that has one glucose attached to the quercetin at position 3 via β-bond, and α-glycosyl isoquercitrins having one or more additional glucoses attached to the glucose residue in the isoquercitrin moiety via α-1,4 bond;
6. The composition as described in any one of 1 to 5 above, which is a food or a beverage;
7. The composition as described in any one of 1 to 5 above, which is a pharmaceutical composition;
8. An agent for enhancing the bodily absorption of sesamin-class compound(s), which contains at least one quercetin glycoside as an active ingredient;
9. Use of at least one quercetin glycoside for producing an agent for enhancing the bodily absorption of sesamin-class compound(s);
10. A method of enhancing the bodily absorption of sesamin-class compound(s), which comprises administering at least one sesamin-class compound and at least one quercetin glycoside; and
11. A method of enhancing the bodily absorption of sesamin-class compound(s), which comprises administering at least one sesamin-class compound and at least one quercetin glycoside, either substantially simultaneously, or successively with an interval provided between the taking of one active ingredient and the administration of the other.

Advantages of the Invention

According to the present invention, the bodily absorbability of sesamin-class compounds can be improved by using them in combination with quercetin glycosides. Hence, the physiological activities of sesamin-class compounds can be exhibited efficiently without increasing the dosage of their administration.

In addition, quercetin glycosides are a class of polyphenol compounds and have not only potent anti-oxidation activity but also various physiological activities including an improvement in the flow of blood. What is more, both sesamin-class compounds and quercetin glycosides originate from plants, so they are extremely safe. Consequently, not only does the present invention improve the absorbability of sesamin-class compounds but, at the same time, it is anticipated to exploit the useful physiological actions of quercetin glycosides while providing foods or beverages as well as pharmaceutical compositions that are safe and can be ingested on a continuous basis.

BEST MODE FOR CARRYING OUT THE INVENTION

The present invention relates to compositions containing sesamin-class compound(s) and quercetin glycoside(s), as well as agents for enhancing the bodily absorption of sesamin-class compound(s).

Sesamin-class Compounds

The sesamin-class compounds as used in the present invention is the collective term for a series of compounds including sesamin, episesamin and their analogs. Examples of the above-mentioned sesamin analogs include the dioxabicyclo [3.3.0]octane derivatives mentioned in JP 4-9331 A. Specific examples of the sesamin-class compounds include sesamin, episesamin, sesaminol, episesaminol, sesamolin, etc. and stereoisomers or racemic bodies of these compounds may be used either independently or as their mixtures. In the present invention, sesamin and/or episesamin can be used with advantage. In addition, the metabolites of sesamin-class compounds (such as those described in JP 2001-139579 A) may be used in the present invention as the sesamin analogs included in the category of sesamin-class compounds of the present invention, on the condition that they exhibit the effects of the present invention.

The sesamin-class compounds to be used in the present invention are not limited in any way by their form, production methods, and the like. If, for example, sesamin is chosen as the sesamin-class compound, sesame oil may be subjected to extraction by a known method (such as the one described in JP 4-9331 A) to obtain sesamin (hereinafter called a sesamin extract or concentrate), which is then used; if desired, a commercial grade of sesame oil (in liquid form) may be used as such. However, one disadvantage of using sesame oil is its low sesamin content (usually less than 1%), so if one attempts to incorporate sesamin in the amount required to attain its physiological actions, the volume per unit dosage of the com- position to be prescribed becomes so excessive as to cause occasional inconvenience to ingestion. In particular, in the case where the composition is formulated for oral administration, the preparation (e.g. tablet or capsule) becomes so bulky as to cause trouble in ingestion. Hence, for the specific reason that the composition need be ingested in a smaller amount, the sesamin extract (or sesamin concentrate) from sesame oil is preferably used. It should be noted here that since the characteristic flavor of sesame oil is sometimes evaluated to be organoleptically undesirable, the sesamin extract (or sesamin concentrate) may be rendered tasteless and odorless by a known means such as treatment with activated clay.

Thus, the sesamin-class compounds that are preferably used are the concentrates of sesamin-class compounds that are enriched in the concentration of sesamin-class compounds by extraction and/or purification from ingredients originating from foods such as sesame oil. The degree of enrichment may be set as appropriate for the kind of sesamin-class compounds to be used or the form of the composition in which the sesamin-class compounds are to be incorporated; preferably used concentrates of sesamin-class compounds are such that the sesamin-class compounds have been enriched to a total content of at least 1% by weight. The total content of sesamin-class compounds in their concentrate is more preferably at least 20% by weight, even more preferably at least 50% by weight, and yet more preferably at least 70% by weight, with one enriched (purified) to 90% by weight and higher being optimum.

Quercetin Glycosides

The quercetin glycosides as used in the present invention is the collective term for a series of compounds that are represented by the following formula (I):

[Chemical Formula 3]

(where $(X)_n$ signifies a sugar chain, and n signifies an integer of 1 or more) and which have a chain of one or more saccharides attached via glycoside bond to the hydroxyl group at position 3 of the quercetin. The saccharide represented by X that is attached to the quercetin via glycoside bond may be exemplified by glucose, rhamnose, galactose, glucuronic acid, etc., with glucose and rhamnose being preferred. In addition, the value of n is not particularly limited as long as it is 1 or more, but it is preferably about 1 to 16, more preferably about 1 to 8. In the present invention, these compounds encompassed in the category of quercetin glycosides may be used independently or, if desired, mixtures of two or more compounds may be used.

Preferred quercetin glycosides of formula (I) for use in the present invention are represented by formula (II):

[Chemical Formula 4]

(where Glc signifies a glucose residue, and m signifies an integer of 0 or 1 or more), and consist of isoquercitrin that has one glucose attached to the quercetin at position 3 via β-bond (isoquercitrin is hereinafter sometimes referred to simply as "IQC"), and respective species of α-glycosyl isoquercitrins that have about 1 to 15 additional glucoses attached to the glucose residue in the IQC moiety via α-1,4 bond. Quercetin glycosides that are used with particular advantage in the present invention are those which have 0 to 7 glucoses attached to the glucose residue in IQC via α-1,4 bond.

The quercetin glycosides to be used in the present invention are in no way limited by their form, methods of production, and the like; for example, extracts obtained by known methods from onion and others that are known to contain quercetin glycosides in large amounts may be used as such; alternatively, synthetic products may also be used. If quercetin glycosides are to be formulated as foods or beverages or pharmaceutical compositions, they are preferably incorporated in effective amounts by using such forms that they have been enriched, purified or otherwise processed to higher contents (i.e., quercetin glycosides in a concentrated or purified form). In this case, enrichment and purification may be performed by known methods. If necessary, quercetin glycosides that have desired sugar chains bound thereto by an enzymatic treatment and the like may also be used. For example, isoquercitrin can be produced by the method described in the pamphlet of WO 2005/030975, namely, a treatment of rutin with naringinase in the presence of a specified edible ingredient. Furthermore, according to WO 2005/030975, isoquercitrin may be treated with glycosyltransferase to yield α-glycosyl isoquercitrins corresponding to a compound of the above formula (II) (where m is an integer of 1 or more).

The quercetin glycosides to be used in the present invention are commercially available from San-Ei Gen F.F.I., INC. under the trade names SANMELIN (registered trademark) AO-1007 and SANMELIN (registered trademark) C-10.

Compositions Containing Sesamin-Class Compound(s) and Quercetin Glycoside(s) and Agents for Enhancing the Bodily Absorption of Sesamin-Class Compound(s)

In the present invention, by combining sesamin-class compounds with quercetin glycosides, the bodily absorbability of sesamin-class compounds is sufficiently enhanced that their physiological activity is exhibited efficiently and, in addition, if the two kinds of compounds are used in health foods and the like, health promotion can be achieved by the physiological actions of the respective ingredients.

The compositions (foods and beverages, pharmaceutical compositions, etc.) of the present invention which contain sesamin-class compounds and quercetin glycosides are not particularly limited with respect to the amounts and proportions in which the sesamin-class compounds and quercetin glycosides are incorporated as long as they are within such a range that the bodily absorption of the sesamin-class compounds is promoted and their physiological activity is exhibited efficiently, and they may be chosen as appropriate for various conditions, such as the form of the compositions and the state of the disease to be treated. Note here that the amount of any quercetin glycoside that is indicated herein is expressed in terms of a value as calculated for the aglycon, quercetin. Specifically, this value can be calculated by first dividing the amount of the quercetin glycoside by its molecular weight to obtain the number of moles of the quercetin glycoside and then multiplying it by the molecular weight of quercetin, 302.24. Thus, to measure this value, a certain quercetin glycoside may be hydrolyzed by a known means such as a glycosidase such as β-glucuronidase (Cellulase Onozuka RS, Yakult) or α-glycosidase (derived from rice), and the number of moles of quercetin contained in the hydrolyzate is measured by a known means such as chromatography, and then multiplied by the molecular weight of quercetin. Herein, the amount of the quercetin glycoside thus calculated for quercetin is sometimes referred to as the value "converted to the amount of quercetin" or "the amount in terms of quercetin."

Particularly in the case of administering the composition to humans (adults), the total amount of sesamin-class compounds to be incorporated in the composition is preferably such that they can be ingested in 1-200 mg, more preferably about 5-100 mg, by an adult per day. The total amount of quercetin glycosides to be incorporated in the composition is such that they can be ingested in 5-200 mg, preferably about 5-100 mg, as the amount in terms of quercetin.

Depending on its total weight, the composition of the present invention may contain sesamin-class compounds in amounts of 1-100 mg, preferably 1-60 mg, more preferably about 3-60 mg. The composition may also contains quercetin glycosides in amounts of 5-200 mg, preferably 5-100 mg, more preferably about 5-60 mg in terms of quercetin.

The total proportion of sesamin-class compounds to be incorporated in the compositions (foods and beverages, pharmaceutical compositions, etc.) of the present invention is preferably at least 1% by weight, more preferably 1-50% by weight, and even more preferably 1-10% by weight, of the total weight of the composition; if the composition of the present invention is in the form of a liquid, the total proportion of sesamin-class compounds relative to the total weight of the composition can be about 0.0002-0.4% by weight, preferably 0.001-0.04% by weight, and more preferably 0.002-0.02% by weight. On the other hand, the total proportion of quercetin glycosides to be incorporated in the composition relative to the total weight of the composition is preferably 0.5-40% by weight, more preferably 0.5-35% by weight, and even more preferably 1-25% by weight, as an amount in terms of quercetin; if the composition of the present invention is in the form of a liquid, the total proportion of quercetin glycosides relative to the total weight of the composition can be 0.001-10% by weight, preferably 0.001-1% by weight, and more preferably 0.001-0.5% by weight, as an amount in terms of quercetin. The liquid referred to above is a water-soluble liquid that is provided as a beverage filled in a container and may be exemplified by health drinks, soft drinks, tea beverages, solutions, suspensions, syrups, etc., as will be described later.

The compositions of the present invention which contain sesamin-class compounds and quercetin glycosides are not limited with respect to the proportions in which the sesamin-class compounds and quercetin glycosides are incorporated; however, if the effect for enhancing the bodily absorption of sesamin-class compounds is desired, the proportion of the total amount of sesamin-class compounds relative to the total amount of quercetin glycosides as converted to the amount of quercetin is at least 1:0.2 or 0.3 by weight, preferably between 1:0.3 and 1:50 by weight, more preferably between 1:0.6 and 1:20 by weight, and even more preferably between 1:0.6 to 1:10 by weight.

The present invention can thusly enhance the bodily absorption of sesamin-class compounds. This effect can typically be verified by measuring the blood concentrations of sesamin-class compounds, as will be described later in Examples 1 to 4.

As will be described in detail in the Examples to be given later, the present inventors confirmed that when sesamin-class compounds in an amount of 10 mg/kg (the amount of sesamin-class compounds (mg) per kilogram of the body weight of an animal) as well as quercetin glycosides in amounts of 15-150 mg/kg (6.1-61.1 mg/kg, as the amount in terms of quercetin) were administered, the bodily absorption of sesamin-class compounds was markedly enhanced in comparison with the case of administering 10 mg/kg of sesamin-class compounds alone.

As described above, by combining sesamin-class compounds with quercetin glycosides, the bodily absorbability of sesamin-class compounds is markedly enhanced. Therefore, the present invention can also be utilized as an agent for enhancing the bodily absorption of sesamin-class compounds that contains quercetin glycosides as an active ingredient.

The agent for enhancing the bodily absorption of sesamin-class compounds that contains quercetin glycosides is such that the proportion and amount in which the quercetin glycosides are to be incorporated as well as the amount in which they are to be ingested can be determined as appropriate based on the numerical values given above for the proportion, amount, etc. in which quercetin glycosides are to be incorporated in the composition containing sesamin-class compounds and quercetin glycosides. In addition, the proportion of sesamin-class compounds relative to an agent for enhancing the bodily absorption that is administered together with the sesamin-class compounds is also the same as specified above for the composition containing sesamin-class compounds and quercetin glycosides.

Foods and Beverages, as Well as Pharmaceuticals

The composition and the agent for enhancing the bodily absorption of the present invention are advantageously provided in the form of foods and beverages (e.g., functional foods, dietary supplements, foods with nutrient function claims, foods for special dietary use, foods for specified health use, nutritional supplements, foods for dietary therapy, health foods, and supplements in general), as well as in the form of pharmaceuticals. Such foods and beverages as well as pharmaceuticals include not only edible or drinkable compositions and pharmaceutical compositions that contain sesamin-class compounds and quercetin glycosides, but also foods and beverages as well as pharmaceuticals that contain or have added thereto the compositions just mentioned above. They also include foods and beverages as well as pharmaceuticals that contain or have added thereto the agent for promoting the bodily absorption of sesamin-class compounds that contain quercetin glycosides as an active ingredient.

Alternatively, the foods and beverages as well as pharmaceuticals may be pet foods processed as feed for pets, other animal feeds, etc. as well as veterinary drugs.

The foods and beverages as well as pharmaceuticals that contain sesamin-class compounds and quercetin glycosides can be used for obtaining the various physiological actions that are considered to be effectively materialized by sesamin-class compounds, including the action of lowering the blood cholesterol and the blood neutral lipid, the action of improving hepatic functions, the action of scavenging active oxygen, the action of inhibiting Δ5-desaturase, the action of suppressing the generation of lipid peroxides, the anti-hypertensive action, the action of preventing sickness from drinking, and the breast cancer suppressing action. In addition, the foods and beverages as well as pharmaceuticals that contain quercetin glycosides and which serve as an agent for enhancing the bodily absorption of sesamin-class compounds can be used for allowing the sesamin-class compounds to exhibit the above-described various physiological actions in an efficient manner.

If the compositions of the present invention are to be provided as foods or beverages, they may be provided in various types including, but not limited to, health foods in such forms as tablets, capsules, powders, granules and health drinks (including solutions and suspensions), as well as soft drinks, tea beverages, dairy products such as yoghurt and lactic acid bacteria beverages, seasonings, processed foods, desserts, and confections (e.g., gums, candies, and jelly).

If the compositions of the present invention are to be used as pharmaceuticals, the mode of administration may be oral or they may be administered in such forms as injection, and known formulations suitable for respective administrations may be employed as appropriate. Formulations suitable for oral administration include, but are not limited to, tablets, capsules, powders, granules, solutions, suspensions, and syrups.

In addition to the sesamin-class compounds and quercetin glycosides, the compositions of the present invention may optionally contain any additives or any ingredients that are used in ordinary foods and beverages as well as pharmaceuticals. Examples of these additives and/or ingredients include not only physiologically active ingredients such as vitamins (e.g. vitamin E and vitamin C), minerals, nutritional ingredients and flavors, but also excipients, binders, emulsifiers, tonicity agents (isotonization agents), buffers, dissolution promoters, antiseptics, stabilizers, antioxidants, colorants, coagulants, coating agents and others that are incorporated in the formulation procedure.

If desired, two preparations, one containing the sesamin-class compounds and the other containing the quercetin glycosides, may be formulated separately and then administered almost simultaneously or, alternatively, one preparation may be first taken and while its efficacy persists, the other preparation is administered; in this way, the action for enhancing the bodily absorption of sesamin-class compounds as intended by the present invention can be obtained. Hence, a kit comprising two components, one being the agent for enhancing the bodily absorption of sesamin-class compound (s) which contains quercetin glycoside(s), and the other being the composition containing sesamin-class compound(s), is also envisaged by the present invention. The respective components separately contained in the kit may be ingested simultaneously, or they may be ingested sequentially or separately.

The kit may have one or more containers for accommodating the above-described components, each of which may be a composition or formulation; such two kinds of components may be accommodated in the same container or they may be accommodated in different containers. Alternatively, such composition(s) or formulation(s) may be accommodated separately in different compartments within the same container that are typically divided by partitions. Any known types of containers may be used, including bottles, bags, and PTP sheets. For example, the kit may be a package containing two bottles or bags that separately accommodate the above-mentioned two kinds of components, each of which may be a composition or formulation. The kit may also contain a PTP sheet that separately accommodates the above-mentioned two kinds of components, each of which may be a composition or formulation (e.g. tablets) in different compartments.

EXAMPLES

The present invention is described in greater detail by means of the following examples, to which the present invention is in no way limited. Any skilled artisan can change or modify the method of the present invention in various ways before they use it and such changes or modifications are also included within the scope of the present invention.

Example 1

SD (IGS) male rats (7-wk old) were purchased from CHARLES RIVER JAPAN INC. and habituated in the test environment for a week; the animals that were seen to grow normally were selected and subjected to the test. The rats fasted overnight were divided into three groups each consisting of 6 heads; the first group (control) were administrated 5 ml/kg of distilled water and 3 ml/kg of an olive oil solution of a 1:1 mixture of sesamin and episesamin (purchased from TAKEMOTO OIL & FAT CO., LTD.; hereinafter sometimes referred to as the "mixture of sesamin-class compounds") at a concentration of 10 mg/3 ml; the second group were administrated 5 ml/kg of a distilled water solution of quercetin glycosides (45 mg/5 ml) and 3 ml/kg of an olive oil solution of the mixture of sesamin-class compounds (10 mg/3 ml); the third group were administrated 5 ml/kg of a distilled water solution of quercetin glycosides (150 mg/5 ml) and 3 ml/kg of an olive oil solution of the mixture of sesamin-class compounds (10 mg/3 ml); each group of the rats were administrated via a feeding tube. Both before the administration and 1, 2, 4, 6, 8, 10 and 24 hours after the administration, blood was sampled from the tail vein of each animal into a heparinized collecting tube and centrifuged (8000 rpm×10 min) to prepare plasma samples. After adding an internal standard (UDESMIN; Funakoshi Co., Ltd.) to the samples, solid-phase extraction was performed with Oasis HLB and the resulting solution was concentrated under vacuum, suspended in methanol, passed through a filter, and subjected to LC-MS/MS for quantification of sesamin. The quantities of the sesamin-class compounds were determined from the ratio between their peak area and that of UDESMIN used as the internal standard. The conditions of LC-MS/MS analysis are shown below. Note that the quercetin glycosides used in Example 1 were a mixture of quercetin glycosides wherein 0-7 glucoses are attached to the glucose in the isoquercitrin moiety via α-bond (the average molecular weight is 740.9) (the mixture was obtained from San-Ei Gen F.F.I., INC.) Also note that the amounts of 45 mg and 150 mg for the quercetin glycosides under test correspond to 18.3 mg and 61.1 mg, respectively, in terms of quercetin.

(HPLC)
Column: Develosil C30-UG-5 (5 μm, 2.0Φ×50 mm; product of Nomura Chemical Co., Ltd.)
Mobile phases: A, distilled water; B, methanol; D, aqueous solution of 100 mM ammonium acetate
Flow rate: 0.25 ml/min
Gradient program: liquid B 55%, and liquid D 10%, isocractic (0-2 min); liquid B 55 to 60%, and liquid D 10 to 10% (2-5 min); liquid B 60 to 85%, and liquid D 10 to 10% (5-7 min)

Figure 1:
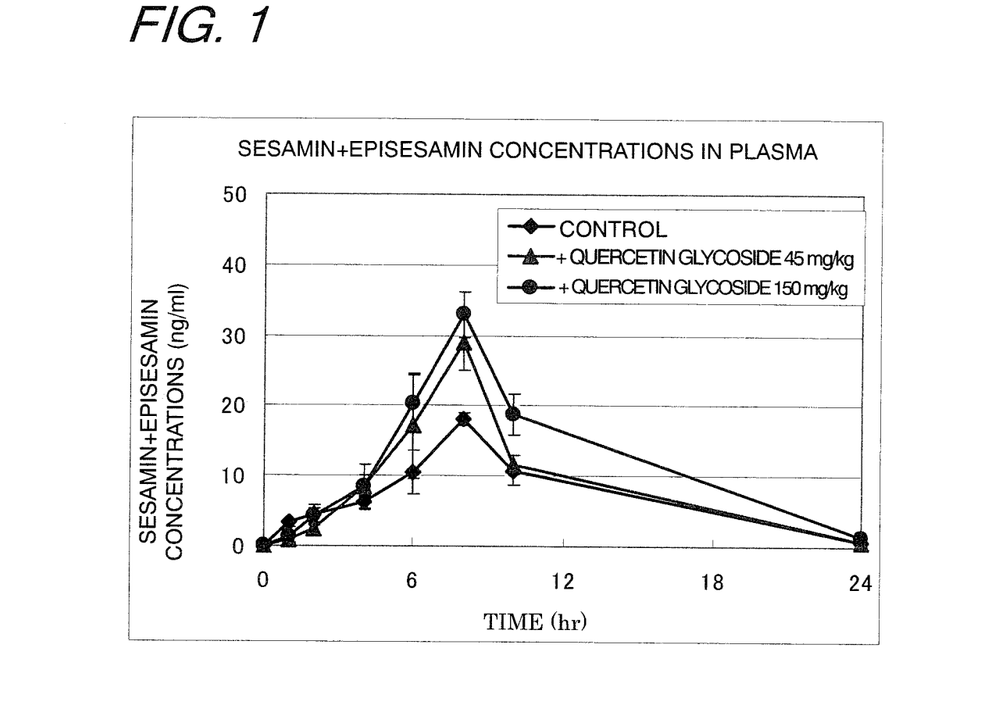
FIG. 1 shows the time-dependent changes in the total sum of the blood sesamin and episesamin concentrations (sesamin+episesamin concentrations) in rats to which a mixture of the sesamin-class compounds was administered either alone or simultaneously with quercetin glycosides.
Figure 2:
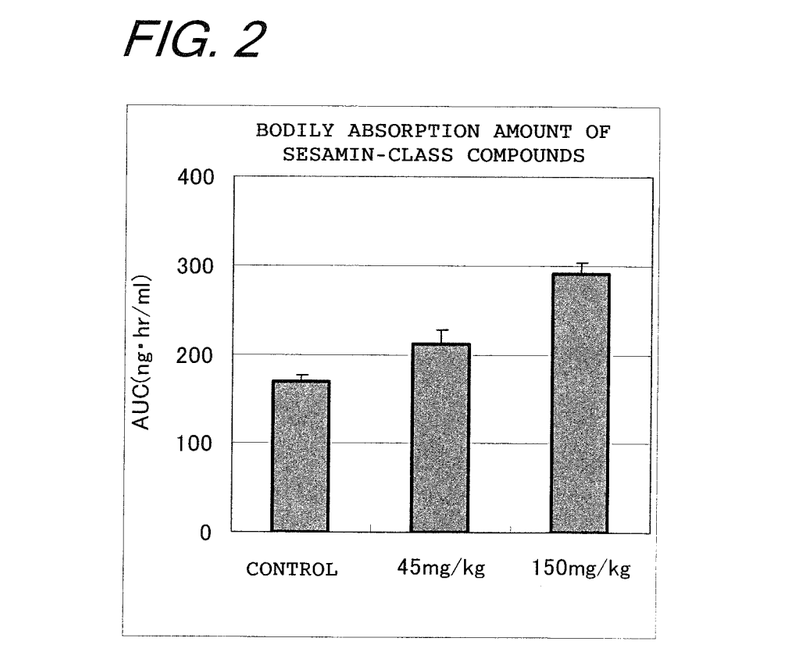
FIG. 2 shows the effect that quercetin glycosides in 45 mg/kg and 150 mg/kg (18.3 mg/kg and 61.1 mg/kg, respectively, as calculated for quercetin) were found to have on the amount of bodily absorption (AUC) of the sesamin-class compounds.

(MS/MS)
Measuring mode: Selective reaction monitoring
Detection: Sesamin (retention time, ca. 5.1 min); precursor ion m/z=372 ($[M+NH_4]^+$), product ion m/z=233
:Episesamin (retention time, ca. 5.4 min); precursor ion m/z=372 ($[M+NH_4]^+$), product ion m/z=233
:UDESMIN (retention time, ca. 2.9 min); precursor ion m/z=369 ($[M-H_2O]^+$), product ion m/z=298
Ionization Method: ESI Method The results are shown in FIGS. 1 and 2. When the mixture of sesamin-class compounds was administered alone, the total maximum blood concentration (Cmax) of the sesamin-class compounds (sesamin and episesamin) was 18.0 ng/ml; on the other hand, when the mixture of sesamin-class compounds and 45 mg/kg of the quercetin glycosides (18.3 mg/kg in terms of quercetin) were ingested simultaneously, the total maximum blood concentration (Cmax) of the sesamin-class compounds rose to 29.1 ng/ml, and when the mixture of sesamin-class compounds and 150 mg/kg of the quercetin glycosides (61.1 mg/kg in terms of quercetin) were ingested simultaneously, the total maximum blood concentration (Cmax) of the sesamin-class compounds rose to 33.0 ng/ml (FIG. 1). This is also true with the amount of bodily absorption of the sesamin-class compounds (AUC); compared to the case where the mixture of the sesamin-class compounds was administered alone, simultaneous ingestion of the quercetin glycosides caused marked increases in AUC, i.e., 1.25 times as much when the dosage was 45 mg/kg (18.3 mg/kg in terms of quercetin), and 1.74 times as much when the dosage was 150 mg/kg (61.1 mg/kg in terms of quercetin) (see FIG. 2).

The foregoing results suggest that by ingesting sesamin-class compounds and quercetin glycosides simultaneously, the bodily absorption amount of sesamin-class compounds increases in a manner dependent on the dose of the quercetin glycosides, enabling potentiation of the various physiological activities of the sesamin-class compounds.

Example 2

In order to determine the minimum necessary amount of quercetin glycosides that was required to increase the amount of absorption of sesamin-class compounds, the dose of the quercetin glycoside was decreased and their effect was tested.

An experiment was conducted as in Example 1, except that the dosage of the quercetin glycoside was varied. Namely, the rats fasted overnight were divided into three groups each consisting of 6 heads; the first group (control) were administrated 5 ml/kg of distilled water and 3 ml/kg of an olive oil solution of the mixture of sesamin-class compounds (10 mg/3 ml); the second group were administrated 5 ml/kg of a distilled water solution of the quercetin glycosides (5 mg/5 ml) and 3 ml/kg of an olive oil solution of the mixture of the sesamin-class compounds (10 mg/3 ml); the third group were administrated 5 ml/kg of a distilled water solution of the quercetin glycosides (15 mg/5 ml) and 3 ml/kg of an olive oil solution of the mixture of the sesamin-class compounds (10 mg/3 ml); each group of the rats were administrated via a feeding tube. Their blood concentrations were measured over time as in Example 1. Note that the amounts of 5 mg and 15 mg for the quercetin glycosides under test correspond to 2.0 mg and 6.1 mg, respectively, if they are converted to the amount of quercetin.

Figure 3:
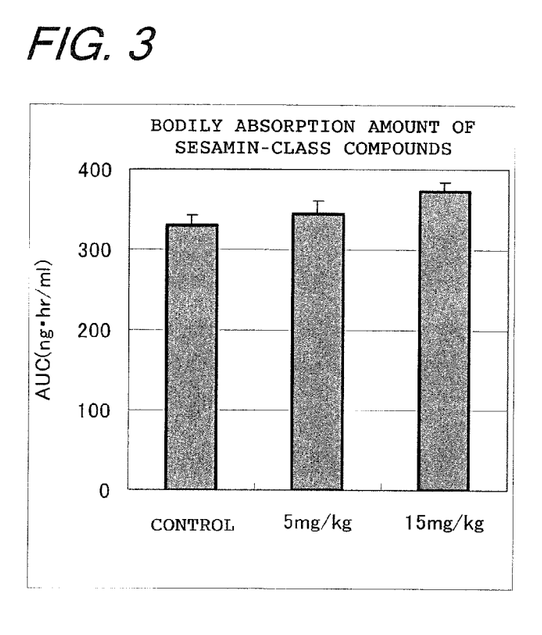
FIG. 3 shows the effect that quercetin glycosides in 5 mg/kg and 15 mg/kg (2.0 mg/kg and 6.1 mg/kg, respectively, as calculated for quercetin) were found to have on the amount of bodily absorption (AUC) of the sesamin-class compounds.

The results of measuring the AUC of the sesamin-class compounds are shown in FIG. 3. When the quercetin glycosides were ingested simultaneously in an amount of 5 mg/kg (2.0 mg/kg in terms of quercetin), the bodily absorption amount of the sesamin-class compounds (AUC) was 1.04 times the value for the control group that ingested the mixture of the sesamin-class compounds alone, and particularly in the case where the quercetin glycosides were ingested simultaneously in an amount of 15 mg/kg (6.1 mg/kg in terms of quercetin), the AUC increased markedly and it was 1.13 times the value for the control group.

Although data is not shown, it was verified that the above-described absorption enhancing effect was equally exhibited on both sesamin and episesamin.

From the foregoing results, it became clear that in order to increase the blood concentration of sesamin-class compounds, a quercetin glycoside must be present in an amount of at least 5 mg (2.0 mg in terms of quercetin) relative to 10 mg of sesamin-class compounds, and that particularly in the case where a quercetin glycoside was used in an amount of 15 mg (6.1 mg in terms of quercetin) or more relative to 10 mg of sesamin-class compounds, a marked absorption enhancing effect was obtained.

Example 3

In order to check to see if the action for improving the bodily absorbability of sesamin-class compounds was characteristic of quercetin glycosides or not, an evaluation was made of the interaction between rutin, a quercetin glycoside having not only glucose but also another saccharide, and sesamin-class compounds, and of the interaction between other flavonoid glycosides and sesamin-class compounds. Using rutin (Funakoshi Corporation) and other flavonoid glycosides (i.e., αG-hesperidin, product of HAYASHIBARA SHOJI, INC., and naringin, product of SIGMA), their effects on the absorption of sesamin-class compounds were tested at concentrations that corresponded to the dose at which the quercetin glycosides proved most effective (150 mg/kg=200 μmol/kg). An experiment was conducted as in Example 1, except that the test substances were varied. Namely, the rats fasted overnight were divided into four groups each consisting of 4 heads; the first group (control) were administrated 5 ml/kg of 0.5% CMC aqueous suspension and 3 ml/kg of an olive oil solution of the mixture of the sesamin-class compounds (10 mg/3 ml); the second group were administrated 5 ml/kg of 0.5% CMC aqueous suspension of αG-hesperidin (200 μmol/5 ml) and 3 ml/kg of an olive oil solution of the mixture of the sesamin-class compounds (10 mg/3 ml); the third group were administrated 5 ml/kg of 0.5% CMC suspension of rutin (200 μmol/5 ml) and 3 ml/kg of an olive oil solution of the mixture of the sesamin-class compounds (10 mg/3 ml); the fourth group were administrated 5 ml/kg of 0.5% CMC suspension of naringin (200 μmol/5 ml) and 3 ml/kg of an olive oil solution of the mixture of the sesamin-class compounds (10 mg/3 ml); each group of the rats were administrated via a feeding tube. The blood concentrations of sesamin and episesamin were measured over time.

Figure 4:
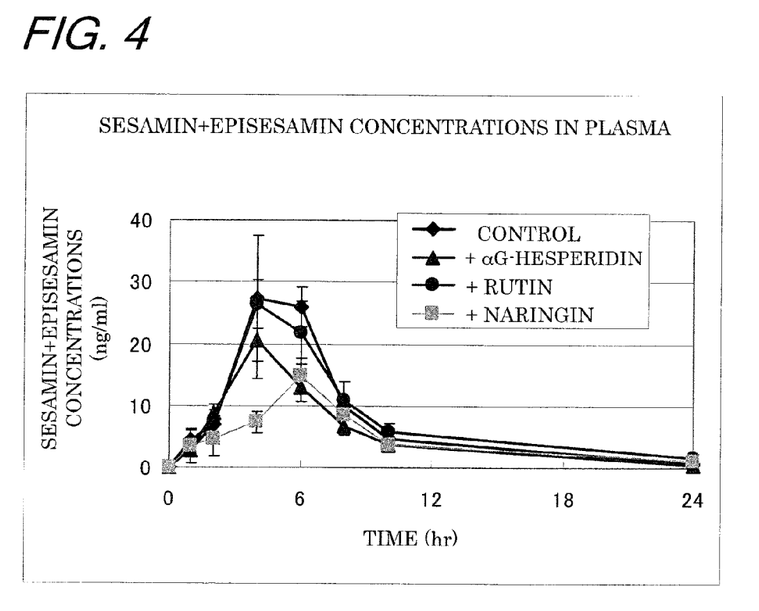
FIG. 4 shows the time-dependent changes in the total sum of the blood sesamin and episesamin concentrations (sesamin+episesamin concentrations) in rats to which a mixture of the sesamin-class compounds was administered either alone or simultaneously with a flavonoid glycoside.
Figure 5:
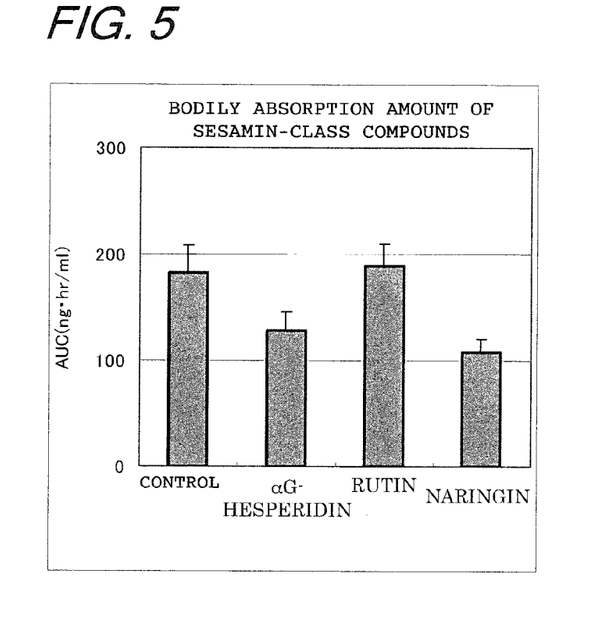
FIG. 5 shows the effect that a variety of flavonoid glycosides were found to have on the amount of bodily absorption (AUC) of the sesamin-class compounds.

The results are shown in FIGS. 4 and 5. The Cmax of sesamin and episesamin was found to decrease when the sesamin-class compounds were used in combination with αG-hesperidin or naringin (FIG. 4). In addition, comparison of the bodily absorption amounts (AUC) of the sesamin-class compounds showed that the amount of bodily absorption in the case of using rutin in combination with the sesamin-class compounds was greater than in the case of the control (1.04 times greater), but that the bodily absorption amount of the sesamin-class compounds decreased to 0.71 times the value for the control when the mixture of the sesamin-class compounds and αG-hesperidin were ingested simultaneously, and to 0.59 times the value for the control when the mixture of the sesamin-class compounds and naringin were ingested simultaneously (FIG. 5).

From the results of Example 4, it was suggested that the action for increasing the bodily absorption amount of sesamin-class compounds is not exhibited by flavonoids in general but is characteristic of quercetin glycosides.

Example 4

Quercetin glycosides are known to have an antioxidant action (see, for example, the official gazette of JP 1-213293 A). In Example 4, in order to check to see if the action for improving the bodily absorbability of sesamin-class compounds would be found in antioxidants in general or not, an evaluation was made of the interaction between vitamin C, a representative antioxidant, and sesamin-class compounds.

Using a vitamin C of Nacali Tesque, Inc., its effect on the absorption of sesamin-class compounds was tested at a concentration that corresponded to the dose at which the quercetin glycosides proved most effective (150 mg/kg=200 μmol/kg). An experiment was conducted as in Example 1, except that the test substance was varied. Namely, the rats fasted overnight were divided into two groups each consisting of 4 heads; the first group (control) were administrated 5 ml/kg of distilled water and 3 ml/kg of an olive oil solution of the mixture of the sesamin-class compounds (10 mg/3 ml); the second group were administrated 5 ml/kg of a distilled aqueous solution of vitamin C (200 μmol/5 ml) and 3 ml/kg of an olive oil solution of the mixture of the sesamin-class compounds (10 mg/3 ml); each group of the rats were administrated via a feeding tube. The blood concentration of sesamin-class compounds was measured over time.

Figure 6:
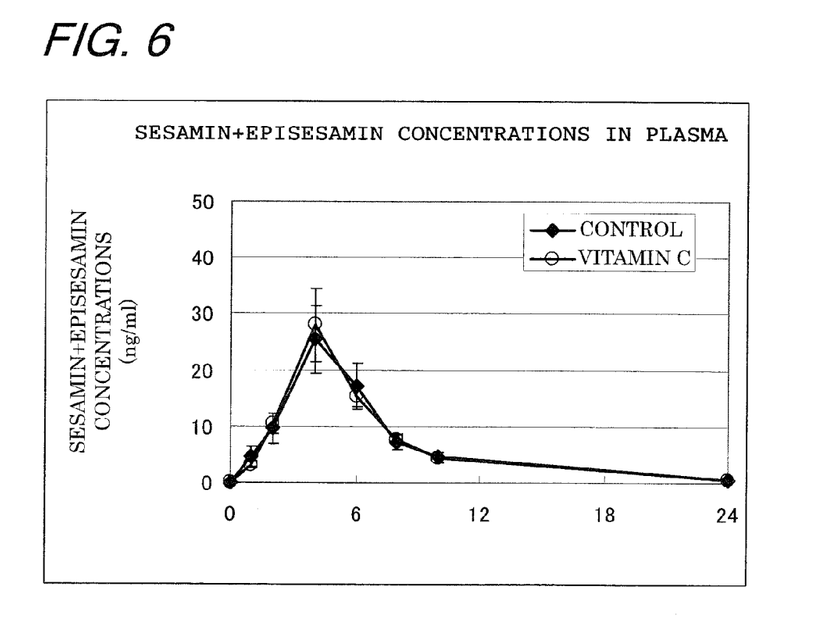
FIG. 6 shows the time-dependent changes in the total sum of the blood sesamin and episesamin concentrations (sesamin+episesamin concentrations) in rats to which a mixture of the sesamin-class compounds was administered either alone or simultaneously with vitamin C.
Figure 7:
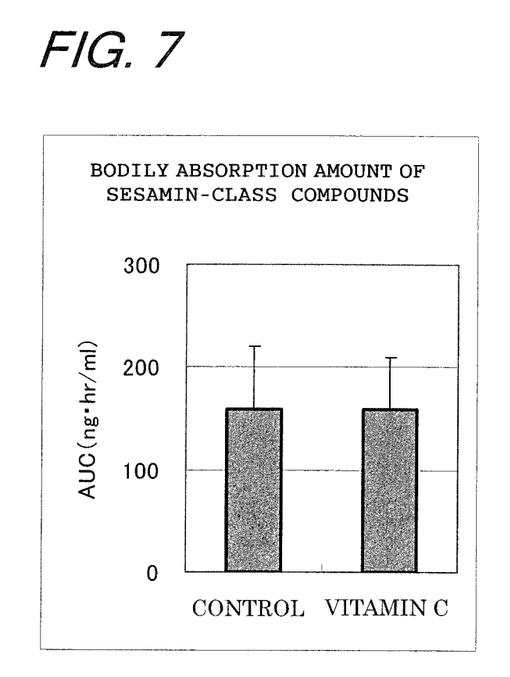
FIG. 7 shows that vitamin C did not influence the amount of bodily absorption (AUC) of sesamin-class compounds.

The results are shown in FIGS. 6 and 7. Even when the mixture of sesamin-class compounds and vitamin C were ingested simultaneously, there were observed no effects on the absorption and disappearance of the sesamin-class compounds, but the blood concentration profile was the same as in the case where the mixture of sesamin-class compounds was administered alone (FIG. 6). In addition, the bodily absorption amount (AUC) of sesamin remained 1.00 times the value for the control even when vitamin C was used in combination with the mixture of sesamin-class compounds, and it was found to have no influence (FIG. 7).

From the results of Example 4, it was suggested that the action for increasing the bodily absorption amount of sesamin-class compounds is not exhibited by water-soluble antioxidants in general but is characteristic of quercetin glycosides.

As shown in Examples 3 and 4, the compounds that were similar to quercetin glycosides in the aspects of structure and action were tested for the action for improving the absorption of sesamin-class compounds, and it was shown that the action of interest is characteristic of the quercetin glycosides.

Example 5

Formulae

| (Formulation 1) Granule | |
|---|---|
| Sesamin | 10 g |
| Quercetin glycosides | 50 g (20 g in terms of quercetin) |
| Tocopherol acetate | 0.5 g |

| (Formulation 1) Granule -continued | |
|---|---|
| Silicic acid anhydride | 41 g |
| Corn starch | 98.5 g |

After uniformly mixing the powder consisting of the above ingredients, 100 ml of a 10% hydroxypropylcellulose solution in ethanol was added and the usual procedure consisting of blending, extruding and drying steps was followed to make granules.

| (Formulation 2) Capsule | |
|---|---|
| Gelatin | 60.0% |
| Glycerin | 30.0% |
| Methyl paraoxybenzoate | 0.15% |
| Propyl paraoxybenzoate | 0.51% |
| Water | q.s. |

A soft capsule shell made of these ingredients was filled with the following composition by the usual method to make soft capsules each weighing 360 mg.

| | |
|---|---|
| Sesamin | 3.5 mg |
| Quercetin glycosides | 10 mg (4.1 mg in terms of quercetin) |
| Vitamin E | 35 mg |
| Glycerol fatty acid ester | 15.0 mg |
| Beeswax | 15.0 mg |
| Wheat germ oil | 219.4 mg |

| (Formulation 3) Tablet | |
|---|---|
| Sesamin | 10 g |
| Quercetin glycosides | 90 g (36.7 g in terms of quercetin) |
| Vitamin E | 50 g |
| Starch | 142 g |
| Sucrose fatty acid ester | 9.0 g |
| Silicon oxide | 9.0 g |

These ingredients were mixed and tableted with a single-action tableting machine to make tablets each having a diameter of 9 mm and weighing 300 mg.

| (Formulation 4) Health Drink | |
|---|---|
| Major taste givers: sodium DL-tartrate | 0.1 g |
| succinic acid | 0.009 g |
| Sweetener: liquid sugar | 800 g |
| Acidifier: citric acid | 12 g |
| Vitamin C | 10 g |
| Sesamin | 1 g |
| Quercetin glycosides | 24.5 g (10 g in terms of quercetin) |
| Vitamin E | 20 g |
| Cyclodextrin | 5 g |
| Emulsifier | 5 g |
| Flavor | 15 ml |
| Potassium chloride | 1 g |
| Magnesium sulfate | 0.5 g |

The invention claimed is:

1. A composition containing at least one sesamin-class compound and at least one quercetin glycoside,
    wherein the sesamin-class compound is selected from the group consisting of sesamin, episesamin, sesaminol, episesaminol, and sesamolin,
    wherein the quercetin glycoside is at least one member selected from the compounds which are represented by the formula (II):

(where m is 0, or an integer of 1 or more), and consist of isoquercitrin that has one glucose attached to the quercetin at position 3 via β-bond, and α-glycosyl isoquercitrins having one or more additional glucoses attached to the glucose residue in the isoquercitrin moiety via α-1,4 bond,
    wherein the total weight of the quercetin glycoside as calculated for quercetin is 0.3 or more relative to the total weight of the sesamin-class compound which is taken as unity.

2. The composition according to claim 1, which is a food or a beverage.

3. The composition according to claim 1, wherein the sesamin-class compound is sesamin and/or episesamin.

4. The composition according to claim 1, wherein m is an integer of 0 to 7.

5. A method of enhancing the bodily absorption of sesamin-class compound(s), which comprises administering a composition containing at least one sesamin-class compound and at least one quercetin glycoside,
    wherein the sesamin-class compound is selected from the group consisting of sesamin, episesamin, sesaminol, episesaminol, and sesamolin,
    wherein the quercetin glycoside is at least one member selected from the compounds which are represented by the formula (II):

(where m is 0, or an integer of 1 or more), and consist of isoquercitrin that has one glucose attached to the quercetin at position 3 via β-bond, and α-glycosyl isoquercitrins having one or more additional glucoses attached to the glucose residue in the isoquercitrin moiety via α-1,4 bond,
    wherein the total weight of the quercetin glycoside as calculated for quercetin is 0.3 or more relative to the total weight of the sesamin-class compound which is taken as unity.

6. The method according to claim 5, wherein the sesamin-class compound is sesamin and/or episesamin.

7. The method according to claim 5, wherein m is an integer of 0 to 7.

* * * * *

UNITED STATES PATENT AND TRADEMARK OFFICE
CERTIFICATE OF CORRECTION

PATENT NO. : 8,653,040 B2  Page 1 of 1
APPLICATION NO. : 12/810635
DATED : February 18, 2014
INVENTOR(S) : Tomimori et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 513 days.

Signed and Sealed this
Twenty-ninth Day of September, 2015

Michelle K. Lee
*Director of the United States Patent and Trademark Office*